United States Patent [19]

O'Rourke et al.

[11] Patent Number: 5,168,367
[45] Date of Patent: Dec. 1, 1992

[54] VARIABLE PATH LENGTH SPECTROPHOTOMETRIC PROBE

[76] Inventors: Patrick E. O'Rourke, 157 Greenwood Dr., Martiney, Ga. 30907; Jerry E. McCarty, 104 Recreation Dr., Aiken, S.C. 29803; Ricky A. Haggard, 1144 Thornwood Drive, North Augusta, S.C. 29891

[21] Appl. No.: 641,978
[22] Filed: Jan. 16, 1991
[51] Int. Cl.⁵ ............................................. G01N 21/05
[52] U.S. Cl. ..................................... 356/246; 250/576
[58] Field of Search ........................ 356/436, 246, 440; 250/576, 227.11

[56] References Cited

U.S. PATENT DOCUMENTS

| 2,649,011 | 8/1953 | Black | 356/246 |
| 4,023,909 | 5/1977 | Ross | 356/436 |
| 4,786,171 | 11/1988 | LeFebre et al. | 356/326 |
| 4,988,155 | 1/1991 | Harner et al. | 356/440 |
| 5,036,194 | 7/1991 | Hazel | 250/227.21 |

FOREIGN PATENT DOCUMENTS 3339950  4/1983  Fed. Rep. of Germany .

Primary Examiner—Vincent P. McGraw
Attorney, Agent, or Firm—Harold M. Dixon; William R. Moser; Richard E. Constant

[57] ABSTRACT

A compact, variable pathlength, fiber optic probe for spectrophotometric measurements of fluids in situ. The probe comprises a probe body with a shaft having a polished end penetrating one side of the probe, a pair of optic fibers, parallel and coterminous, entering the probe opposite the reflecting shaft, and a collimating lens to direct light from one of the fibers to the reflecting surface of the shaft and to direct the reflected light to the second optic fiber. The probe body has an inlet and an outlet port to allow the liquid to enter the probe body and pass between the lens and the reflecting surface of the shaft. A linear stepper motor is connected to the shaft to cause the shaft to advance toward or away from the lens in increments so that absorption measurements can be made at each of the incremental steps. The shaft is sealed to the probe body by a bellows seal to allow freedom of movement of the shaft and yet avoid leakage from the interior of the probe.

19 Claims, 1 Drawing Sheet

VARIABLE PATH LENGTH SPECTROPHOTOMETRIC PROBE

BACKGROUND OF THE INVENTION

1. Field of the Invention

The present invention relates to spectrophotometry. In particular the present invention relates to probes used in making spectrophotometric measurements of fluids. The United States Government has rights in this invention pursuant to Contract No. DE-AC09-89SR18035 between the U.S. Department of Energy and Westinghouse Savannah River Company.

2. Discussion of Background

Spectrophotometry is widely used in industrial applications for measuring concentrations of chemical compounds. Usually a sample is obtained from one or more locations in the chemical processing system and analyzed in a laboratory.

Analysis of the sample can proceed in several ways. However, one way is to measure the absorption of light by the chemical sample at one distance and then repeat the measurement at a second, different distance. In the late 1800's, the fundamentals of concentration as a function of absorption and path length were laid down by Bier. Thus, it is well known that altering path length so more than one measurement can be taken of absorption can yield concentration data.

Several devices perform these measurements. See for example the spectral analysis apparatus described by LeFebre, et al. in U.S. Pat. No. 4,786,171. Lefebre, et al. provide a light source and optical fiber wave guides to shine light through a sample of a chemical and back to an analyzer. A servo mechanism or linear stepper motor changes the path length of light through the sample. A mirror or prism can be used to reflect light from one optical fiber to the other.

See also the apparatus of Ross described in U.S. Pat. No. 4,023,909 and that in German patent DE 3,339,950 A1 owned by Hartmann & Braun.

The difficulty arises in performing these measurements accurately and repeatably in situ in the chemical processing system itself. For in situ measurements, ruggedness, reliability and compactness are essential. If the chemicals of interest are corrosive or radioactive, seals must be effective in preventing leakage. There is a need for an in situ spectrophotometric probe that reliably provides accurate data in hostile chemical environments.

SUMMARY OF THE INVENTION

According to its major aspects, the present invention is a probe for use with a spectrophotometer and a light source in making spectrophotometric measurements in a fluid. The probe has a probe body with an interior. Two optical fibers terminate in the probe body, with one of the fibers coming from the light source and the other going to the spectrophotometer. The fibers are coterminous and parallel inside the probe body. A collimating lens directs the light from the fiber coming from the light source onto a reflector and directs the reflected light onto the fiber going to the spectrophotometer. There is thus established a light path from the light source through the first optical fiber, through the lens, to the reflector, back through the lens to the second optical fiber and on to the spectrophotometer.

The probe body has a passage for the fluid to pass between the reflector and the lens so that the light from the source shines through the fluid which can absorb light in accordance with the concentration of chemical substances comprising the fluid.

The reflector is a polished end of a shaft connected to a linear stepper motor that receives pulses from a source of pulses. The shaft is sealed to the probe body by a bellows seal. The motor turns in response to the pulses to moving the shaft forward to backward in increments, changing the path length over which the light travels. Spectrophotometric measurements are made at any of the incremental distances and used to determine the concentration of the fluid in the probe body.

It is a feature of the present invention that the distance from the lens to the reflector can be changed incrementally and repeatably. That is, the precise distance between lens and reflector can be changed to alter the path length traveled by the light and any distance can be selected for remeasurement. The advantage of this feature is that the path length differences can be known precisely for accurate and repeatable measurements. Thus the concentrations, which can be derived from the absorbance, can also be precisely known. Furthermore, if a series of measurements are taken at a set of incremental distances, uncertainty in any particular measurement can be statistically reduced.

Another feature of the present invention is the positioning of the optical fibers coterminally and in adjacent relation along with the use of a lens and reflector. The advantage of this feature is that the probe can be compact. The lens and reflector allow the path traveled by the light to be "folded" and to travel twice through the passage for the fluid. A compact probe can more easily fit into an industrial processing system without interference.

An additional feature having the advantage of compactness but also ruggedness is the polishing of the end of the shaft to serve as the reflector of the light back through the lens. No separate component is required and the shaft, which can be made of metal, will be more durable and scratch resistant than glass. Furthermore, reflecting the light reduces the size of the probe for a given path length.

Still another feature of the present invention is the use of a bellows to seal the shaft to the probe body. A bellows seal allows the shaft to move but prevents leakage of the fluid from the probe interior.

Other features and advantages of the present invention will be apparant to those skilled in the art of spectrophotometry from a careful reading of the Detailed Description of a Preferred Embodiment accompanied by the following drawings.

DETAILED DESCRIPTION OF A PREFERRED EMBODIMENT

Figure 1:
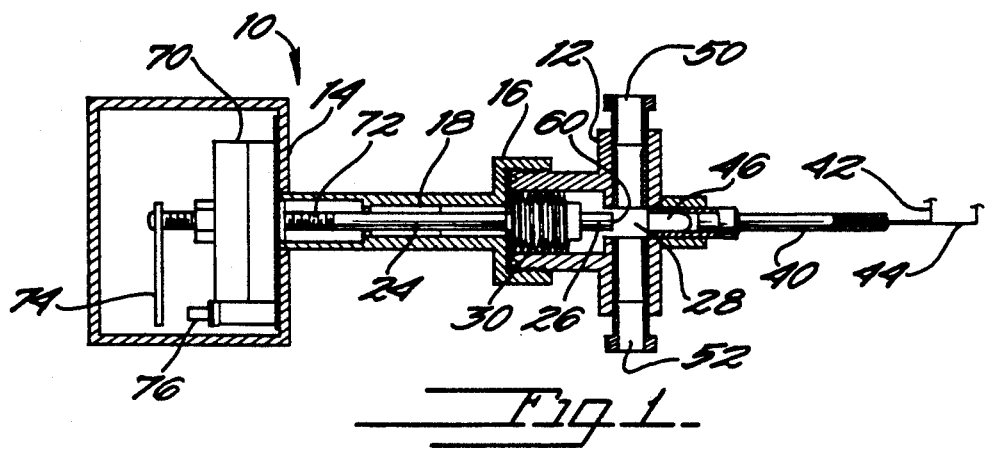
FIG. 1 is a side cross sectional view of a preferred embodiment of the present invention.
Figure 2:
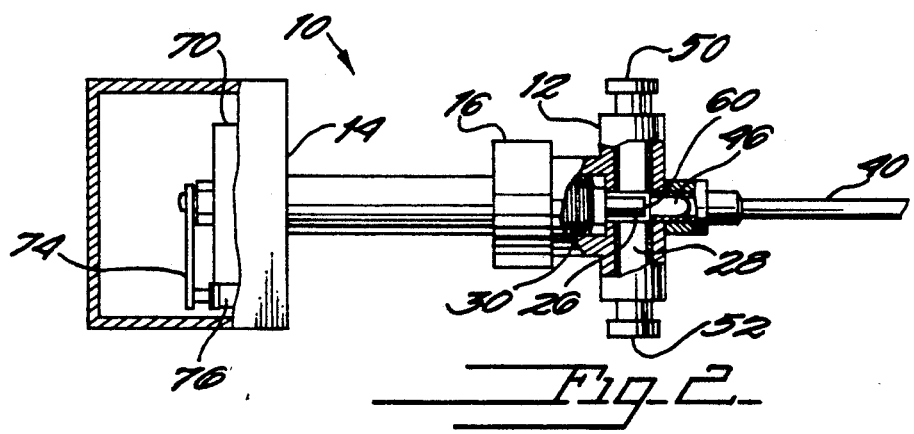
FIG. 2 is another side cross sectional view of a preferred embodiment of the present invention showing the mirrored surface against the lens.

Referring now to FIGS. 1 and 2, there is illustrated a probe, generally indicated by the reference character 10, comprising a probe body 12 and a motor assembly 14. Motor assembly 14 is attached to probe body 12 by a threaded housing 16 having a bore 18 therethrough. Inside bore 18 is a shaft 24 having an end 28 that penetrates into the interior 28 of probe body 12. Shaft 26 is sealed to probe body 12 by means of a bellows 30. The bellows allows shaft 26 to move without causing a leaking from the interior of probe body.

Opposing the end of shaft 26 is an optical fiber cable 40 having two optical fibers 42, 44 therein. One optical fiber 42 comes from a source of light (not shown); the other optical fiber 44 goes to a spectrophotometer (also not shown). Light is carried by first optical fiber 42 from the light source to the interior 28 of probe 10. Light from the interior 28 of probe 10 is carried by second optical fiber 44 back to the spectrophotometer for analysis. Optical fibers 42 and 44 are coterminous and parallel. A lens 46 is positioned next to the ends of optical fibers 42, 44. Lens 46 is preferably a collimating lens, such as a planoconvex lens oriented with the convex side toward optical fibers 42, 44 and the plane side facing toward shaft 26.

Two ports 50 and 52 allow access for a fluid to the interior 28 of probe body 12. One port 52 serves as an inlet and the other serves as the outlet for the fluid. Ports 50, 52 are positioned so that the fluid is at least for a portion of the time between shaft 26 and lens 46.

The end of shaft 26 is ground and polished on the end 60 so that it will reflect light. Light from first optical fiber 42 is collimated by lens 46 and directed toward end 60 where it will be reflected back to lens 46 and directed to second optical fiber 44.

In motor assembly is a linear stepper motor 70 having a threaded shaft 72 aligned and attached to shaft 26. As motor 70 operates, threaded shaft 72 is moved linearly toward or away from probe body 12. Thus shaft 26 will move with threaded shaft 72 in response to the operation of linear stepper motor 70. Stepper motor 70 receives pulses from a controller (not shown) which determine the angle stepper motor 70 turns. The pitch of the threads of threaded shaft 72 will determine how far shaft 26 moves toward or away from lens 46.

At one end of threaded shaft 72 is a shaft position indicator 74 which will engage a limit switch 76. Comparing FIGS. 1 and 2, it will be seen that shaft 24 can be advanced by stepper motor 70 from a first position wherein the reflecting surface 60 is away from lens 46 and position indicator 74 is away from limit switch 76, to a second position where reflecting surface 60 is very nearly touching lens 46, preferably 0.005 inches, having been stopped when position indicator 74 touches limit switch 76. A total gap of one-half inch is sufficient to provide the range needed for making a few measurements of high and low concentrations of most chemical fluids. More importantly, the advancement of stepper motor 70, which is controlled in the usual manner with pulses, can advance shaft 26 incrementally. Measurements of absorption can be made at any increment between the extreme positions of shaft 26. Increments of 1 millimeter are preferred for most applications and at least two or three measurements are sufficient to determine the concentration.

Figure 3:
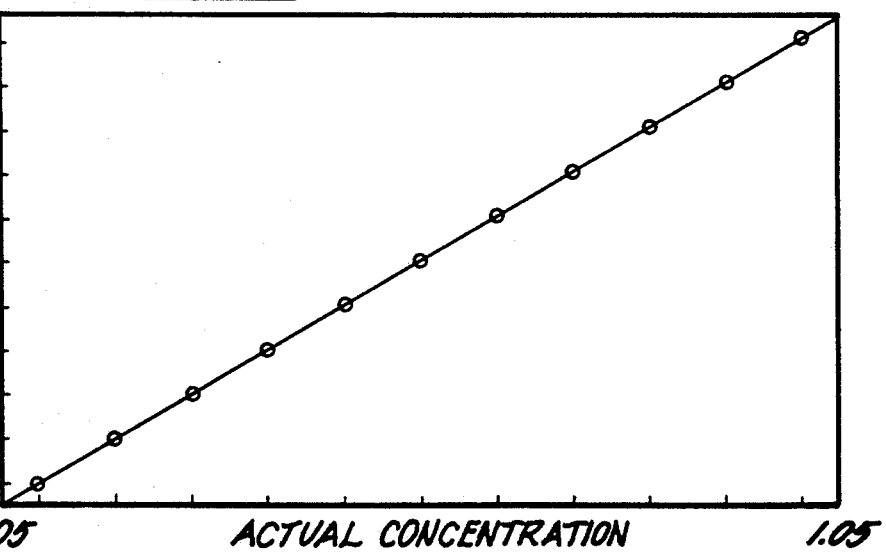
FIG. 3 is a graph showing the results of a test of a prototype device made according to the preferred embodiment of FIGS. 1 and 2.

Being able to make incremental measurements has several advantages. First, in high concentrations, measurements at closer increments may be necessary because light might not pass through the highly concentrated fluid easily. Also, a series of measurements at increments will serve to verify each data point. FIG. 3 is a graph of actual concentration versus concentration predicted based on absorption data acquired at eleven data points using a device built according to the preferred embodiment described herein. In addition to being accurate predictors of true concentration, the linearity of the data confirms that the data was collected at equally-spaced, known increments; no data is errant as a result of a larger incremental distance movement.

In use, fluid would be admitted in inlet 50 and flow through interior 28 to outlet 52. Light from a light source would be carried by first optical fiber 42 to interior 28 of probe body 12. The light would be directed through the fluid to reflecting surface 60 by lens 46 where it would be reflected back to lens 46. Pulses from the controller would cause linear stepper motor 70 to turn. A first measurement would be made at any distance between lens 46 and reflecting surface 60 of shaft 26. Linear stepper motor 70 would receive one or more pulses to move shaft 26 incrementally forward or backward. A second measurement would be taken; a second incremental movement of shaft 26 would be made and a third measurement taken.

It will be apparent to those skilled in the art of spectrophotometry that many changes and substitutions can be made in the preferred embodiment described herein without departing from the spirit and scope of the invention which is to be defined by the appended claims.

What is claimed is:

1. A probe for making spectrophotometric measurements in a fluid with a spectrophotometer and a light source, said probe comprising:

a probe body having an interior;

first means for carrying light from said light source to said interior of said probe body, said first carrying means having a first end and a second end;

second means for carrying light to said spectrophotometer from said interior of said probe body, said second carrying means having a first end and a second end;

a shaft, said shaft positioned in said interior of said probe body, said shaft spaced apart from said first and said second carrying means and aligned therewith;

means for moving said shaft;

means for sealing said shaft to said probe body so that fluid does not pass from said interior of said probe body;

means for reflecting light, said reflecting means carried by said shaft;

lens means for directing light received from said second end of said first carrying means to said reflecting means and for directing light received from said reflecting means to said second end of said second carrying means; and an inlet formed in said probe body and in communication with said probe interior so that said fluid may enter said probe interior; and an outlet formed in said probe body and in communication with said probe interior so that said fluid may exit said probe interior.

2. The probe as recited in claim 1, wherein said lens means further comprises a collimating lens.

3. The probe as recited in claim 1, wherein said shaft has an end with a surface, said end opposing said lens means, and said reflecting means is a portion of said surface.

4. The probe as recited in claim 1, wherein said moving means further comprises:

a motor; and means for advancing said shaft toward or away from said lens in response to operation of said motor.

5. The probe as recited in claim 4, wherein said shaft has an end with a surface, said end opposing said lens means, and said reflecting means is a portion of said surface, and wherein said moving means further comprises:

a motor; and means for advancing said shaft toward or away from said lens in response to operation of said motor.

6. The probe as recited in claim 1, wherein said first carrying means is a first optical fiber having a first end and an opposing second end, said first end of said first optical fiber receiving light from said light source, said second end of said first optical fiber positioned in said interior of said probe body, said first optical fiber carrying said light from said light source to said second end of said first optical fiber; and wherein said second carrying means is a second optical fiber having a first end and an opposing second end, said second end of said second optical fiber receiving light from said interior of said probe body, said first end in optical connection with said spectrophotometer, said second ends of said first and said second optical fibers positioned so as to be adjacent and coterminous.

7. The probe as recited in claim 6, wherein said lens means further comprises a collimating lens.

8. The probe as recited in claim 6, wherein said shaft has an end with a surface, said end opposing said lens means, and said reflecting means is a portion of said surface.

9. A probe for use with a spectrophotometer and a light source in making spectrophotometric measurements in a fluid, said probe comprising:

a probe body having an interior;

a first optical fiber having a first end and an opposing second end, said first end of said first optical fiber receiving light from said light source and said second end of said first optical fiber positioned in said interior of said probe body;

a second optical fiber having a first end and an opposing second end, said second end of said second optical fiber receiving light from said interior of said probe body and said first end in optical connection with said spectrophotometer, said second end of said second optical fiber positioned parallel and adjacent to said second end of said first optical fiber, whereby said first optical fiber carries said light from said light source to said second end of said first optical fiber and said second optical fiber carries said light from said interior to said first end of said second optical fiber;

a shaft, said shaft positioned in said interior of said probe body, said shaft spaced apart from said first and second optical fibers and aligned therewith;

means for moving said shaft;

means for sealing said shaft to said probe body so that fluid does not pass from said interior of said probe body;

means for reflecting light, said reflecting means carried by said shaft; and a lens, said lens opposing said reflecting means so that said lens directs light from said second end of said first optical fiber to said reflecting means and from said reflecting means to said second end of said second optical fiber.

10. The probe as recited in claim 9, wherein said sealing means is a bellows.

11. The probe as recited in claim 9, wherein said shaft has an end with a surface, said end opposing said lens means, and said reflecting means is a portion of said surface.

12. The probe as recited in claim 9, wherein said lens is a planoconvex lens having a convex side and a plane side, said convex side facing said second ends of said first and second optical fibers and said plane side facing said reflecting means.

13. The probe as recited in claim 9, wherein said moving means further comprises:

a motor; and means for advancing said shaft toward or away from said lens in response to the operation of said motor.

14. The probe as recited in claim 12, wherein said moving means further comprises:

a motor; and means for advancing said shaft toward or away from said lens in response to the operation of said motor.

15. A probe for use with a spectrophotometer and a light source in making spectrophotometric measurements in a fluid, said probe comprising:

a probe body having an interior;

a first optical fiber having a first end and an opposing second end, said first end receiving light from said light source, and said second end transmitting said light into said interior of said probe body;

a second optical fiber having a first end and an opposing second end, said first end in optical connection with said spectrophotometer so that light from said second end of said first optical fiber must travel a distance through said fluid to reach said second end of said second optical fiber, said second end of said second optical fiber receiving light from said interior of said probe body;

a shaft, said shaft positioned in said interior of said probe body, said shaft spaced apart from said first and said second optical fibers and aligned therewith;

means for sealing said shaft to said probe body so that fluid does not pass from said interior of said probe body;

a reflector, said reflector carried by said shaft;

a collimating lens, said lens opposing said reflector so that said lens directs light from said second end of said first optical fiber to said reflector and from said reflector to said second end of said second optical fiber;

a motor; and means for advancing said shaft toward or away from said lens in response to the operation of said motor.

16. The probe as recited in claim 15, wherein said sealing means further comprises a bellows encircling said shaft, said bellows expanding as said reflecting means moves toward said second ends of said first and second optical fibers and said bellows contracting as said reflecting means moves away from said second ends of said first and second optical fibers.

17. The probe as recited in claim 15, wherein said lens is a planoconvex lens having a convex side and a plane side, said convex side facing said second ends of said first and second optical fibers and said plane side facing said reflecting means.

18. The probe as recited in claim 15, further comprising means for producing pulses, wherein said motor is a linear stepper motor responsive to said pulses.

19. The probe as recited in claim 17, wherein said sealing means further comprises a bellows encircling said shaft, said bellows expanding as said reflecting means moves toward said second ends of said first and second optical fibers and said bellows contracting as said reflecting means moves away from said second ends of said first and second optical fibers; and wherein said shaft has an end with a surface, said opposing said lens means, and said reflecting means is a portion of said surface.

* * * * *